United States Patent [19]

Duchene et al.

[11] Patent Number: 5,550,223
[45] Date of Patent: Aug. 27, 1996

[54] LIPOPROTEIN I (OMPI) OF PSEUDOMONAS AERUGINOSA

[75] Inventors: Michael Duchene, München; Ulrich von Specht, Ambach; Horst Domdey, Neuried, all of Germany

[73] Assignee: Behringwerke Aktiengesellschaft, Marburg, Germany

[21] Appl. No.: 242,059

[22] Filed: May 13, 1994

Related U.S. Application Data

[63] Continuation of Ser. No. 12,797, Feb. 2, 1993, abandoned, which is a continuation of Ser. No. 400,810, Aug. 30, 1989, abandoned.

[30] Foreign Application Priority Data

Sep. 1, 1988 [DE] Germany .......................... 38 29 616.0

[51] Int. Cl.$^6$ ...................................................... C07H 21/04
[52] U.S. Cl. ............................................. 536/23.7; 935/9
[58] Field of Search ............................................. 536/23.7

[56] References Cited

U.S. PATENT DOCUMENTS 4,358,535   11/1982   Falkow et al. ............................... 435/6

FOREIGN PATENT DOCUMENTS 0101039   2/1984   European Pat. Off. ................. 435/7.1

OTHER PUBLICATIONS

Mizuno et al., J. Biochem. 85:115–122 (1979).
Strom et al., J. Bact. 165 (2): 367–372 (Feb. 1986).
*Dictionary of Microbiology & Molecular Biology*, Singleton et al, eds., John Wiley & Sons, Chuhester, 1987. p. 270.
Duchene et al., Journal of Bacteriology 171: 4130–4137 (1989).
Cornelis et al., "Cloning and Analysis of the Gene for the Major Outer Membrane Lipoprotein . . . ", Molecular Microbiology, 3: 421–428 (1989).
Lebel et al., "Cloning and Express. of the Lipoprotein . . . ", Abstracts of the Annual Mtg. of the Amer. Soc. for Microbiol., 89: 106: D–142 (1989).
Mizuno et al., "Isolation and Characterization of a Major Outer Membrane Protein . . . ", Chemical Abstracts, 90: 212: 116676n (1979).
Mizuno et al., "Isolation and Characterization of Major Outer Membrane Proteins . . . ", Chemical Abstracts, 91: 205: 188261s (1979).
Marget et al., "Cloning and Characterization of cDNAs Coding for the Heavy and Light Chains of a Monoclonal . . . ", Gene, 74: 335–345 (1988) European Search Report, Jul. 23, 1990.
A.–M. Frischauf, et al., J. Mol. Biol., 1983, vol. 170, pp. 827–842.
M. Duchene, et al., J. Bacteriol., 1988, vol. 170, No. 1, pp. 155–162.
F. Sanger, et al., Proc. Natl. Acad. Sci. USA, 1977, vol. 74, No. 12, pp. 5463–5467.
K. Nakamura, et al., Cell, 1979, vol. 18, pp. 1109–1117
H. E. Gilleland, Jr., et al., Infection and Immunity, 1984, vol. 44, No. 1, pp. 49–54.
R. E. W. Hancock, et al., J. Infectious Diseases, 1984, vol. 149, No. 2, pp. 220–226.
S. Inouye, et al., J. Bacteriol., 1976, vol. 127, No. 1, pp. 555–563.
G. Köhler, et al., Nature, 1975, vol. 256, pp. 495–497.
T. Maniatis, et al., Molecular Cloning: A Laboratory Manual, 1982, published by Cold Spring Harbor Laboratory, Table of Contents.
F. Bolivar, et al., Gene, 1977, vol. 2, pp. 95–113.
C. Yanisch–Perron, et al., Gene, 1985, vol. 33, pp. 103–119.
E. Chen, et al., DNA, 1985, vol. 4, No. 2, pp. 165–170.

*Primary Examiner*—Stephanie W. Zitomer
*Attorney, Agent, or Firm*—Finnegan, Henderson, Farabow, Garrett & Dunner, L.L.P.

[57] ABSTRACT

The gene for the outer membrane protein lipoprotein I (OMPI) of *Pseudomonas aeruginosa* ATCC 33354 has been sequenced, and the amino acid sequence has been deduced. This makes it possible to obtain this protein and immunogenic part-sequences thereof in the quantity and purity necessary for use for the preparation of vaccines.

1 Claim, No Drawings

LIPOPROTEIN I (OMPI) OF PSEUDOMONAS AERUGINOSA

This application is a continuation, of pending prior application Ser. No. 08/012,797 filed Feb. 2, 1993, now abandoned, which is a continuation of prior application Ser. No. 07/400,810 filed Aug. 30, 1989 now abandoned.

BACKGROUND OF THE INVENTION

*Pseudomonas aeruginosa* is a microorganism which occurs ubiquitously and is regarded as a "problem microbe" in human medicine. Its prime target is debilitated patients and it can frequently be controlled by antibiotic therapy only with difficulty. At particular risk are patients in intensive care units and paraplegics as well as people who have suffered burns or are exposed to an increased risk of burns, such as firemen or steelworkers. In all these cases there is the prospect of preventing infection by active immunization. Lipoprotein I (OMPI) is, like porin F (OMPF), a major constituent of the outer membrane of *P. aeruginosa* and, for this reason, is likewise potentially suitable as constituent of a vaccine.

SUMMARY OF THE INVENTION

The invention is based on the complete characterization of the gene for OMPI from *P. aeruginosa*, serotype 6, ATCC 33354. The DNA sequence and the amino acid sequence deduced therefrom are depicted in the table, with the amino acid sequence in the three-letter code being arranged under the relevant base triplets, and the signal peptide being emphasized by italic letters.

For this purpose, the proteins of the outer membrane were obtained from *P. aeruginosa,* and monoclonal antibodies were obtained therefrom by classical methods.

Genomic DNA was isolated from the strain and purified, and a lambda EMBL3 gene bank was set up as described (A.-M. Frischauf et al., J. Mol. Biol. 170 (1983) 827–842; M. Duchêne et al., J. Bacteriol. 170 (1988) 155–162). This gene bank was plated out and material from the resulting plaques was transferred to nitrocellulose membranes. A monoclonal antibody which is specific for lipoprotein I of *P. aeruginosa* was used to detect the plaque which expressed small amounts of lipoprotein I. This entailed the antibody-antigen reaction being visualized with the aid of a second antibody coupled to alkaline phosphatase, and of a suitable color reaction. The gene coding for lipoprotein I was located on a DNA segment which was 15 kb in size and which was contained in the positive lambda phage, and it was subsequently localized to a TaqI fragment 626 bp in size. Both strands of the DNA were completely sequenced by the Sanger principle (Sanger et al., Proc. Natl. Acad. Sci. USA 74 (1977) 5463–5467). The corresponding amino acid sequence was deduced from the DNA sequence obtained in this way. The N terminus of the mature protein was deduced by comparison with the corresponding *E. coli* protein in which the mature protein likewise starts with a cysteine residue which is located in the same sequence association Gly-Cys-Ser-Ser (K. Nakamura and M. Inouye, Cell 18 (1979) 1109–1117) as in *P. aeruginosa.*

The isolation of the gene now allows the preparation of lipoprotein I and immunogenic part-sequences of this protein in the quantity and purity necessary for use for the preparation of vaccines.

Hence the invention relates to lipoprotein I (OMPI) having the amino acid sequence shown in the table, to the DNA coding therefor, whose protein-coding strand is depicted in the table, to immunogenic part-sequences of lipoprotein I, to polyclonal and monoclonal antibodies obtained with lipoprotein I and immunogenic part-sequences of this protein, and to the corresponding sera, as well as to diagnostic aids which contain such antibodies or corresponding nucleotide sequences and to diagnostic methods using such diagnostic aids, as well as to processes of genetic manipulation for the preparation of OMPI or immunogenic part-proteins.

Furthermore, the invention opens up a way of passive immunization using human monoclonal antibodies. The invention therefore also relates to the use of antigens obtained according to the invention for inducing lymphocytes to produce corresponding monoclonal antibodies, and for testing lymphocytes for the production of such antibodies.

The working up, purification, immunization and obtaining of the sera and antibodies can be carried out by methods known per se. Reference may be made, for example, to M. E. Gilleland et al., Infection and Immunity 44 (1984) 49–54; R. E. W. Hancock et al., J. Infectious Diseases 149 (1984) 220–226; S. Sawada et al., J. Infectious Diseases 150 (1984) 570–576.

DESCRIPTION OF THE PREFERRED EMBODIMENT

The invention is explained in detail in the examples which follow. Unless indicated otherwise, parts and percentages relate to weight.

EXAMPLE 1

Obtaining lipoprotein I:

Lipoprotein I is obtained by following the procedure of Inouye et al. (J. of Bacteriology 127 (1976) 555–563).

EXAMPLE 2

Obtaining monoclonal antibodies against lipoprotein I:

Purified lipoprotein I is injected in Freund's adjuvant or Al(OH)$_3$ intraperitoneally into Balb/c mice. Dissolved antigen is used for a booster after 6 weeks. The antibody titer is determined one week later by ELISAs. Further injections are carried out if the immune response is inadequate. 10 µg of dissolved antigen are used for intravenous boosting of the mice 3 days before cell fusion. The spleen cells are fused with NS1 cells by standard methods (of G. Köhler and C. Milstein, Nature 256 (1975) 495–497). After selection in HAT medium, single colonies grow in the microwells and their culture supernatants are in turn tested for antibodies against lipoprotein I in an ELISA. Positive colonies are subcloned. The antibodies are obtained from culture supernatants and from ascites induced in Balb/c mice and are purified and characterized by conventional biochemical methods.

EXAMPLE 3

Obtaining and characterizing lipoprotein I DNA
Construction of a gene bank from *P. aeruginosa*:

The construction of the gene bank is published (M. Duchêne et al., J. Bacteriol. 170 (1988) 155–162) and was carried out accordingly.

Screening of the gene bank for lipoprotein I sequences:

Recombinant phages are plated out in a density of 500 pfu (plaque forming units) on an NM539 bacterial lawn and incubated overnight. The phage plaques are further incubated at 37° C. for 6 hours and thus transferred to nitrocellulose membranes. The positive plaques are identified by their content of lipoprotein I, entailing the filters first being incubated with the monoclonal antibody 6A4 and then the positive antibody-antigen reaction being identified using a second antibody and an enzymatic color reaction with alkaline phosphatase.

Sequence analysis of the lipoprotein I gene and its flanking regions:

A large culture (1l) of one of the isolated phages is cultivated, and DNA is prepared therefrom (Manjarls et al., Molecular Cloning, Cold Spring Harbor Publications, 1982). The latter is cleaved with the restriction enzyme SalI, and the resulting restriction fragments are shotgun subcloned into pBR322 (Bolivar et al., Gene 2 (1977) 95–113) and subsequently into pUC19 (Yanisch-Perron et al., Gene 33 (1985) 103–119). In this case lipoprotein I (OMPI) is likewise expressed in sufficient quantity in the transformed E. coli cells, so that positive transformants can be recognized with an antibody reaction. The smallest subclone which expresses the protein is the clone pITaq. Plasmid DNA is isolated from this clone and, after ExoIII and ExoVII digestion (Yanisch-Perron et al., see above), sequenced by the method of Chen and Seeburg (DNA 4 (1985) 165–170). The clone has a TaqI insert which is 626 bp in size and which contains the complete sequence coding for lipoprotein I (OMPI). This sequence is depicted in the table.

EXAMPLE 4

Expression of lipoprotein I:

Since the promoter which guides the transcription of the lipoprotein I gene in *P. aeruginosa* is very similar to the *E. coli* consensus promoter, the protein is expressed in all the plasmids containing the complete sequence of the lipoprotein I transcription unit which have been investigated to date.

Lipoprotein I is obtained by isolating it, by the method of Inouye et al. cited above, from a culture of *E. coli* cells transformed with the plasmid pITaq.

EXAMPLE 5

Preparation of antisera:

Healthy adults who have no allergies, diabetes, immunodeficiency diseases, anemias or skin diseases in their medical history are immunized with lipoprotein I expressed heterologously, or part-sequences thereof. The vaccination is carried out on days 1, 8 and 15. Three weeks after the last injection, blood is taken from the volunteer candidates and is tested for hepatitis B surface antigen as well as for HIV antigens. Only donated plasma with a negative reaction is pooled, fractionated under controlled sterile conditions and packaged.

TABLE

Sequence of lipoprotein I from *Pseudomonas aeruginosa*. The coding region is depicted with the amino acid residues in the three-letter code. The signal peptide is printed in italics.

```
1                               20                              40
ATG AAC AAC GTT CTG AAA TTC TCT GCT CTG GCT CTG GCT GCT GTT
Met Asn Asn Val Leu Lys Phe Ser Ala Leu Ala Leu Ala Ala Val 60                              80
CTG GCC ACC GGT TGC AGC AGC CAC TCC AAA GAA ACC GAA GCT CGT
Leu Ala Thr Gly Cys Ser Ser His Ser Lys Glu Thr Glu Ala Arg 100                             120
CTG ACC GCT ACC GAA GAC GCA GCT GCT CGT GCT CAG GCT CGC GCT
Leu Thr Ala Thr Glu Asp Ala Ala Ala Arg Ala Gln Ala Arg Ala 140                             160                         180
GAC GAA GCC TAT CGC AAG GCT GAC GAA GCT CTG GGC GCT GCT CAG
Asp Glu Ala Tyr Arg Lys Ala Asp Glu Ala Leu Gly Ala Ala Gln 200                             220
AAA GCT CAG CAG ACC GCT GAC GAG GCT AAC GAG CGT GCC CTG CGC
Lys Ala Gln Gln Thr Ala Asp Glu Ala Asn Glu Arg Ala Leu Arg

240
ATG CTG GAA AAA GCC AGC CGC AAG TAA TAG
Met Leu Glu Lys Ala Ser Arg Lys  *   *
```

We claim:

1. An isolated DNA coding for the outer membrane protein lipoprotein I (OMPI) of *Pseudomonas aeruginosa*, having the nucleotide sequence:

```
1                           20
ATG AAC AAC GTT CTG AAA TTC TCT GCT CTG
Met Asn Asn Val Leu Lys Phe Ser Ala Leu
            40                          60
GCT CTG GCT GCT GTT CTG GCC ACC GGT TGC
Ala Leu Ala Ala Val Leu Ala Thr Gly Cys
                        80
AGC AGC CAC TCC AAA GAA ACC GAA GCT CGT
Ser Ser His Ser Lys Glu Thr Glu Ala Arg
            100                         120
CTG ACC GCT ACC GAA GAC GCA GCT GCT CGT
Leu Thr Ala Thr Glu Asp Ala Ala Ala Arg
                        140
GCT CAG GCT CGC GCT GAC GAA GCC TAT CGC
Ala Gln Ala Arg Ala Asp Glu Ala Tyr Arg
            160                         180
AAG GCT GAC GAA GCT CTG GGC GCT GCT CAG
Lys Ala Asp Glu Ala Leu Gly Ala Ala Gln
```

\* \* \* \* \*